United States Patent [19]

Van Haften et al.

[11] Patent Number: 5,221,319
[45] Date of Patent: Jun. 22, 1993

[54] DRY, WATER-SOLUBLE, SUBSTITUTED PHENOXY AND/OR BENZOIC ACID HERBICIDAL COMPOSITIONS AND METHOD OF PREPARING SAME

[75] Inventors: John L. Van Haften, Leawood; Roger P. Cahoy, Overland Park, both of Kans.

[73] Assignee: PBI-Gordon Corporation, Kansas City, Mo.

[21] Appl. No.: 745,866

[22] Filed: Aug. 16, 1991

[51] Int. Cl.$^5$ .............. A01N 25/12; A01N 33/06; A01N 37/38; A01N 37/40
[52] U.S. Cl. .................. 504/144; 71/DIG. 1; 504/116; 504/323; 504/324; 504/322; 504/145
[58] Field of Search ............ 71/115, 116, 117, DIG. 1

[56] References Cited

U.S. PATENT DOCUMENTS

| | | | |
|---|---|---|---|
| 4,015,970 | 4/1977 | Hennart | 71/DIG. 1 |
| 5,022,182 | 6/1991 | Anderson | 47/48.5 |
| 5,022,917 | 6/1991 | Allan | 71/DIG. 1 |

Primary Examiner—Glennon H. Hollrah
Assistant Examiner—S. Mark Clardy
Attorney, Agent, or Firm—Hovey, Williams, Timmons & Collins

[57] ABSTRACT

A dry, water-soluble, substituted phenoxy and/or benzoic acid herbicide is prepared by dry blending the herbicide in acid form with a dry solid solubilization medium selected from the group consisting of diammonium phosphate, dipotassium phosphate, and disodium phosphate. At least about 1.15 moles of the medium are provided for each mole of active herbicidal agent in the initially dry blended mixture.

31 Claims, No Drawings

DRY, WATER-SOLUBLE, SUBSTITUTED PHENOXY AND/OR BENZOIC ACID HERBICIDAL COMPOSITIONS AND METHOD OF PREPARING SAME

BACKGROUND OF THE INVENTION

1. Field of the Invention

This invention relates to water-soluble herbicidal compositions in dry powdered form which include herbicidally active substituted phenoxy and/or benzoic acids that alone are not readily soluble in water.

2. Description of the Prior Art

Those herbicidal agents registered for use by commercial applicators are generally sold in concentrated form for economy of transport, and then diluted by the applicator either at a central distribution center, or less frequently at the point of use. The majority of effective herbicides and plant growth regulators are foliarly absorbed and therefore, to be effective, must be applied to the foliage of the target pest species. Other herbicides are root absorbed and the product must be applied in a manner as to be available to the roots of the target. This is commonly accomplished by spraying a dilute water solution, or dispersion of the desired pesticide on the vegetation to be treated. Most herbicides are therefore marketed as either (1) liquid or dry water-soluble formulations, (2) liquid, water emulsifiable formulations, or (3) solid or liquid water dispersible formulations. The concentrated formulations are diluted to the required effective concentration by the person doing the spray application. Thus, in order to obtain optimum effectiveness and to minimize agitation and other mechanical suspension requirements, water-soluble formulations are normally preferred.

Because of the difficulties of manufacturing a dry, soluble form of herbicide, most dry formulations are simply dispersible forms of essentially insoluble active ingredients. Typical examples of formulations are (1) wettable powders, (2) water dispersible granules, or (3) dry flowables. Formulations of these types depend heavily on surfactants and grinding techniques to provide a dry formulation of active ingredients that can be temporarily dispersed or suspended in water for spray application. Even when a dispersion can initially be obtained in water, the time of full dispersion is usually limited, thus requiring stirring, agitation with air, or other mechanical mixing. Dispersions of this type present additional problems in that the material tends to clog spray nozzles and other distribution components, and require the user to prepare smaller than desired batches in order to minimize application problems.

Because of the problems associated with attempting to prepare the dry powdered herbicide, suppliers have resorted in some instances to dissolution of the active ingredient in an organic solvent such as mineral spirits or the like. The concentrated formulation, containing suitable surfactants, is then diluted with water to form a dispersion that again usually necessitates some type of agitation to maintain the phases substantially homogeneous for a useful period of time.

In instances where the herbicides are dissolved in a solvent for shipment as a concentrate, the solvent presents health and physical hazards to the manufacturer as well as the user, the solvents add to the overall cost of the product, and the solvent agent is oftentimes phytotoxic to desirable plant species.

The wettable powders and solvent dissolved herbicides are frequently packaged in plastic containers and disposal of these plastic packages is becoming increasingly difficult from an environmental standpoint.

Substituted phenoxy and/or benzoic acid herbicides such as (2,4-dichlorophenoxy)acetic acid [2,4-D], 4-(2,4-dichlorophenoxy)butanoic acid [2,4-DB], ($\pm$)-2-(4-chloro-2-methylphenoxy)propanoic acid [MCPP], (4-chloro-2-methylphenoxy)acetic acid [MCPA], ($\pm$)-2-(2,4-dichlorophenoxy)propanoic acid [dichlorprop], 3,6-dichloro-2-methoxybenzoic acid [dicamba], and 3-amino-2,5-dichlorobenzoic acid have long been used to control unwanted vegetation.

These substituted phenoxy and/or benzoic acid herbicides are white crystalline solids with very low vapor pressures and low water solubilities. They are soluble only in alkaline solutions or polar organic solvents.

Phenoxy and/or benzoic acid herbicides are available commercially as acid, ester, alkali metal, and amine salt formulations that can also be applied as mixtures with other herbicides. The alkali metal and especially the amine salt formulations are preferred because they are the most water-soluble and can be more readily applied as aqueous sprays. However, the esters must be applied either as emulsions in water, or as solutions in organic solvents such as oils. 2,4-D for example, is an insoluble crystalline material having a $pK_a$ of approximately 2.6. For ease of application, 2,4-D is normally converted to a water-soluble amine or mineral salt by the manufacturer and then dissolved by the applicator in a water carrier before use.

However, water-soluble substituted phenoxy and/or benzoic acid salts exhibiting herbicidal activity are difficult to prepare in a dry state. Soluble salts such as potassium or sodium or dimethylamine must be first prepared in water or a solvent and then the solvent removed. This requires special equipment, is energy intensive, and frequently generates undesirable waste products. As a consequence, most dry forms of herbicide that are marketed are not of a soluble type but rather are merely dispersible forms of the essentially insoluble herbicide acid which are distributed as a wettable powder or a wettable, dispersible granule. Although both inorganic and organic salt forms are commercially available, the most common salt form is the dimethylamine salt of the substituted phenoxy or substituted benzoic acid herbicide. Typical formulations range from about 20% to 50% active ingredient concentrations in water or solvent solutions.

SUMMARY OF THE INVENTION

The present invention relates to a method of preparing dry, water-soluble, substituted phenoxy and/or benzoic acid herbicides which are in acid form. The invention also concerns dry phenoxy and/or benzoic acid herbicidal powders which may be dissolved in water at concentrations providing from at least about 0.1% to at least about 2½% by weight of the active herbicide in the final herbicidal solution.

A dry herbicidal product is preferred over a liquid concentrated herbicide for a number of reasons. Dry formulations are more stable to temperature variations encountered in storage and shipping. For example, freezing can destabilize liquid products interfering with the effectiveness of the herbicide. Similarly, high storage temperatures can lead to solvent losses when an organic solvent is used to dissolve the agent or cause hydrolysis when water is a solvent, thereby adversely affecting active ingredient concentrations.

Dry herbicidal formulations are less dangerous than liquid products. Package leakage during handling is much less likely. If accidentally punctured, dry package leakage is much less severe and easier to clean up than a liquid product. Also, personnel protection is easier to accomplish with dry products because the material cannot as easily splash into the eyes or skin of the applicator. Spills of solvent containing formulations are potentially flammable, further militating against the use of solvents for dissolving the herbicide.

The ease of packaging is significantly enhanced with dry products over liquid formulations and packaging flexibilities are greatly enhanced. Paper containers or wax treated packages can be used, as well as plastic containers. With liquids, specially treated plastic containers or glass containers are normally required. Paper or cardboard packages can be compressed and disposed of much easier than plastic, glass or metal containers.

Transportation costs of dry products are potentially less expensive than is the case where a liquid carrier must also be transported. Although a number of concentrated liquid products having a fairly high active ingredient content are in commercial use, many formulations are sold in the 20-30% active ingredient range with the remainder of the product being water along with a small amount of dispersing agents or product appearance or handling enhancers.

The dry, water-soluble, substituted phenoxy and/or benzoic acid herbicides of the subject invention are prepared by dry blending the herbicidal agent with a substantially solid solubilization medium for the herbicidal agent which is selected from the group consisting of diammonium phosphate, dipotassium phosphate and disodium phosphate. A sufficient amount of the phosphate solubilization medium is provided in the dry blended mixture in relationship to the quantity of herbicidal agent combined therewith to cause the dry blended mixture to substantially dissolve in water during preparation of a herbicidal solution which contains an adequate proportion of the herbicidal agent to provide from about 0.1% to about 2½% by weight of the active herbicide in the herbicidal solution.

A sufficient amount of the phosphate solubilization medium is dry blended with the dry substituted phenoxy and/or benzoic acid herbicidal agent to provide at least about 1 mole and preferably about 1.15 moles of the phosphate medium for each mole of active herbicidal agent in the dry blended mixture.

The water-soluble substituted phenoxy and/or benzoic acid herbicides are easily manufactured by dry blending the ingredients in powdered form. No unusual manufacturing techniques are required such as grinding to very fine sizes or classification procedures normally necessary to obtain a suitable dispersible product. Product raw material costs are comparable to widely used organic amine phenoxy and/or benzoic acid herbicide formulations currently being marketed. The raw materials are all commercially available and readily obtainable at competitive prices. In addition to the active herbicidal ingredients, the dry blended water-soluble substituted phenoxy and/or benzoic acid herbicide contains nitrogen, phosphorous or potassium ingredients. These are all potentially useful as nutrients to non-susceptible species.

DETAILED DESCRIPTION OF THE INVENTION

A quantity of a substantially solid herbicidal agent selected from the group consisting of substituted herbicidally active phenoxy acids and substituted herbicidally active benzoic acids, which are not readily soluble in water is added to an amount of a substantially solid solubilization medium for the herbicidal agent and selected from the group consisting of diammonium phosphate, dipotassium phosphate and disodium phosphate. Examples of useful phenoxy and/or benzoic acid herbicides are (2,4-dichlorophenoxy)acetic acid [2,4-D], 4-(2,4-dichlorophenoxy)butanoic acid [2,4-DB], (±)-2-(4-chloro-2-methylphenoxy)propanoic acid [MCPP], (4-chloro-2-methylphenoxy)acetic acid [MCPA], (±)-2-(2,4-dichlorophenoxy)propanoic acid [dichlorprop], 3,6-dichloro-2-methoxybenzoic acid [dicamba], and 3-amino-2,5-dichlorobenzoic acid. The phenoxy and/or benzoic acid herbicides may be used alone or as combinations thereof. Preferred formulations include about 50 weight percent of the active herbicidal acid or combinations thereof.

The herbicidal agent and the phosphate solubilization medium are dry blended to produce a substantially homogeneous mixture thereof. This dry blended mixture may be packaged in paper containers, or other suitable packages, without further processing such as pulverization, extended grinding, or critical classification. However, the particle size is preferably small enough to permit relatively rapid wetting when added to water. At least about 1 mole and preferably about 1.15 moles of the solubilization medium is provided for each mole of active herbicidal agent in the dry blended mixture.

EXAMPLE I

The following ingredients were dry blended:

| Ingredients | % Active Ingredients | Weight % Reagents | Makeup for Grinding of 500 Grams - In Grams | HLPC (High Performance Liquid Chromatography Analysis) |
| --- | --- | --- | --- | --- |
| 1. 2,4-D Acid - Tech. Grade - 98% | 31.16 | 31.80 | 159.0 | 31.02 |
| 2. MCPP Acid - Tech. Grade - 94.5% | 15.70 | 16.61 | 83.1 | 15.50 |
| 3. Dicamba - Tech. Grade - 88% | 3.14 | 3.57 | 17.9 | 3.11 |
| 4. Sodium Lignosulfonate - Marasperse CBOS-4 - Borrgaard | | 1.00 | 5.0 | |

| Ingredients | % Active Ingredients | Weight % Reagents | Makeup for Grinding of 500 Grams - In Grams | HLPC (High Performance Liquid Chromatography Analysis) |
| --- | --- | --- | --- | --- |
| Industries | | | | |
| 5. DAP - Diammonium Phosphate - Reagent Grade - 98% | | 46.02 | 230.0 | |
| 5. 8μ Precipitated Silica Powder | | 1.00 | 5.0 | |

Ingredients 1–5 inclusive were dry blended under conditions producing an average particle size of about 50 μ and then placed in a capped glass container. Thereafter, the precipitated silica was added as a coating agent to prevent the product from picking up excessive moisture from the atmosphere.

A prepared aqueous sample containing 2.0 weight percent of the 50% active herbicide powder yielded a clear solution within two minutes. It was not necessary to heat or agitate the product to maintain the ingredients in solution while sitting on a shelf for several days at room temperature. Tests of the dry blended material dissolved in water yielded clear solutions at levels of 0.5%, 1%, 2%, and 4 weight percent. Cloudiness started to appear at a level above about 5 weight percent, and 10 weight percent samples were found to be at least partially insoluble. Weight percent in this respect means 1 gram of the active dry powder for each 99 milliliters of tap water. Normal herbicide application concentrations range from about ½ weight percent of the active acid to about 2% of the active acid.

It has been determined through laboratory testing that technical grade diammonium phosphate may be used in preparing the dry blended water-soluble substituted phenoxy acid/substituted benzoic acid fertilizer composition. The molecular weight of diammonium phosphate is 132.06 and when calculated on 100% basis, a chemical analysis yields 21.22% nitrogen, 23.45% phosphorous and 3.73% $P_2O_5$. Technical grade diammonium phosphate usually has a density of about 60–64 lbs/cu. ft. The pH of a 1% solution is 8.0 and a typical screen analysis yields: Cumulative Retention on 20 Tyler Standard Screen 24–50% Cumulative Retention on 35 Tyler Standard Screen 70–85% Cumulative Retention on 65 Tyler Standard Screen 83–95% Cumulative Retention on 100 Tyler Standard Screen 91–98% Cumulative Retention on 200 Tyler Standard Screen 95.99%

Diammonium phosphate is the preferred solubilization medium because it is a commonly available agricultural chemical, it is less expensive than dipotassium phosphate or disodium phosphate, it has the lowest molecular weight thereby minimizing the amount required in the formulation and it contributes ammonia as well as phosphorous to non-susceptible plants.

The next preferred solubilization medium is disodium phosphate because it has a lower molecular weight than potassium phosphate, thus permitting use of a lesser amount of the additive.

EXAMPLE II

A mixture comprising 3.25 g of technical grade 2,4-D acid (96%), 1.69 g of MCPP acid (93%), 0.37 g of dicamba (86%), 0.1 g of sodium lignosulfonate, and 4.59 g of commercially available disodium phosphate (anhydrous) were ground to a fine, dry powder (about 50 μ) in a laboratory analytical mill. The mixture was transferred to a capped glass container. A 2 g sample of the 50% active herbicide powder was added to a glass stoppered graduated cylinder which contained 98 milliliters of city water. The stoppered cylinder was twice inverted and allowed to stand on the bench top at ambient temperature. By visual inspection, all solids had dissolved within 15 minutes of mixing. The clear aqueous solution was light brown in color.

EXAMPLE III

A mixture comprising 1.62 g of technical grade 2,4-D acid (96%), 0.84 g of MCPP acid (93%), 0.18 g of dicamba (86%), 0.1 g of sodium lignosulfonate, and 7.26 g of dipotassium phosphate (anhydrous) were ground to a fine powder in a laboratory analytical mill. The mixture was transferred to a capped glass container. A prepared aqueous sample containing 2.0 weight percent of the 25% active herbicide powder yielded a clear solution within two minutes. Preparation of the clear solution did not require heating or agitation.

Useful herbicidal compositions in accordance with this invention may be prepared by combining on a parts by weight basis:

EXAMPLE IV 32.4 parts of technical grade 2,4-D (100% basis)

14.5 parts of MCPP (100% basis)
2.1 parts of dicamba (100% basis)
45 parts of diammonium phosphate (98%)

EXAMPLE V 50 parts of MCPA (100% basis)
45.4 parts of disodium phosphate (anhydrous)

EXAMPLE VI 50 parts of MCPA (100% basis)
45.9 parts of diammonium phosphate (98%)

EXAMPLE VII 50 parts of dicamba (100% basis)
40.7 parts of diammonium phosphate (98%)

EXAMPLE VIII 50 parts of 2,4-D (100% basis)
45.9 parts of diammonium phosphate (98%)

Two parts of each of the compositions set out in Examples IV to VIII inclusive when added to 98 parts of water, yielded a clear solution within two minutes. The herbicidal agent and the phosphate solubilization medium may be ground separately and then blended, or ground together. The dry blended product has a particle size from about 50 μ to about 100 μ with the preferred size being about 50 μ.

The dry, water-soluble, substituted phenoxy and/or benzoic acid herbicides of the invention are preferably applied to susceptible flora at rates of from about 3 to about 4 pounds of the dry powder (containing 50% active herbicidal agents) in 20 to 240 gallons of water per acre. Thus, 3 to 4 parts of dry powder are provided in 160 to 1920 parts of water for each acre of coverage.

We claim:

1. A method of preparing a dry, water-soluble, substituted phenoxy and/or benzoic acid herbicide powder composition consisting essentially of the steps of:
   providing a first quantity of dry, powder particles of a substantially solid herbicidal agent selected from the group consisting of herbicidally active phenoxy acids and substituted herbicidally active benzoic acids, which are not readily soluble in water;
   providing a second quantity of dry, solid powder particles consisting essentially of a solubilization medium for the herbicidal agent and selected from the group consisting of diammonium phosphate, dipotassium phosphate and disodium phosphate,
   said first and second quantities of the herbicidal agent and the solubilization medium being the predominate constituents of the composition,
   there being at least one mole of solubilization medium for each mole of herbicidal agent; and
   dry blending the herbicidal agent and the solubilization medium in powdered form without changing the physical state of the particles to retain the discrete particulate character of each of said first and second quantities of said particles, and in the absence of chemical reaction between said herbicidal agent and said solubilization medium to produce a relatively uniform dry mixture thereof,
   a sufficient quantity of the phosphate solubilization medium being provided in the dry blended mixture in relationship to the quantity of herbicidal agent combined therewith to cause the powdered dry blended mixture to substantially dissolve in water during preparation by the applicator of a herbicidal solution which contains an adequate proportion of the herbicidal agent to provide from about 0.1% to about 2½% by weight of the active herbicidal agent in the herbicidal solution.

2. A method a set forth in claim 1 wherein the powdered dry blended admixture includes a mixture of substituted phenoxy acid and substituted benzoic acid herbicides.

3. A method as set forth in claim 1 wherein said active substituted phenoxy acid herbicidal agent is 2,4-dichlorophenoxy acetic acid.

4. A method as set forth in claim 1 wherein said active substituted phenoxy acid herbicidal agent is 4-(2,4-dichlorophenoxy)butanoic acid.

5. A method as set forth in claim 1 wherein said active substituted phenoxy acid herbicidal agent is (±)-2-(4-chloro-2-methylphenoxy)propanoic acid.

6. A method as set forth in claim 1 wherein said active substituted phenoxy acid herbicidal agent is (4-chloro-2-methylphenoxy)acetic acid.

7. A method as set forth in claim 1 wherein said active substituted phenoxy acid herbicidal agent is (±)-2-(2,4-dichlorophenoxy)propanoic acid.

8. A method as set forth in claim 1 wherein said active substituted benzoic acid herbicidal agent is 3,6-dichloro-2-methoxybenzoic acid.

9. A method as set forth in claim 1 wherein said active substituted benzoic acid herbicidal agent is 3-amino-2,5-dichlorobenzoic acid.

10. A method as set forth in claim 1 wherein a sufficient quantity of the phosphate medium is present in the dry blended mixture to provide at least about 1.15 moles of the medium for each mole of active herbicidal agent in the dry blended mixture.

11. A method as set forth in claim 1 wherein is included the step of providing a mixture of said herbicidally active agents for dry blending with the phosphate medium.

12. A method as set forth in claim 1 wherein is included the step of incorporating an anti-caking agent in the dry blended mixture.

13. A method of preparing a phenoxy and/or benzoic acid herbicide solution consisting essentially of the steps of:
   adding to a volume of water, a dry powdered herbicidal composition containing
      a first quantity of dry, powder particles of a substantially solid herbicidal agent selected from a group consisting of substituted herbicidally active phenoxy acids and substituted herbicidally active benzoic acids, which alone are not readily soluble in water, and
      a second quantity of dry, solid powdered particles of a solubilization medium for the herbicidal agent and selected from the group consisting of diammonium phosphate, dipotassium phosphate and disodium phosphate,
      said first and second quantities of the herbicidal agent and the solubilization medium being the predominate constituents of the composition, having been subjected only to dry blending in powdered form without changing the physical state of the particles to retain the discrete particulate character of each of said first and second quantities of said particles, and in the absence of chemical reaction between said herbicidal agent and said solubilization medium,
      there being a sufficient quantity of the phosphate medium present to provide at least about one mole thereof for each mole of active herbicidal agent in the dry blended mixture;
   adding a sufficient quantity of the powdered dry blended admixture of the herbicidal agent and the phosphate solubilization medium to the volume of water to cause the powdered dry blended mixture dissolved in the water to provide from about 0.1% to about 2½% by weight of the active herbicidal agent in the herbicidal solution; and
   agitating the water containing the herbicidal agent and the solubilization medium for a time period sufficient to effect substantial dissolution of the agent and the medium in the volume of water.

14. A dry, water-soluble substituted phenoxy and/or benzoic acid herbicide powder composition consisting essentially of:
   a dry blended admixture of
      a first quantity of dry, powder particles of a substantially solid herbicidal agent selected from the group consisting of substituted herbicidally active phenoxy acids and substituted herbicidally active benzoic acids, which alone are not readily soluble in water, and
      a second quantity of dry, powder particles of a solubilization medium for the herbicidal agent and selected from the group consisting of diammonium phosphate, dipotassium phosphate and disodium phosphate, said first and second quantities of the herbicidal agent and the solubilization medium being the predominate constituents of the composition, there being at least one mole of solubilization medium for each mole of herbicidal agent, said herbicidal agent and the solubilization medium having been dry blended in powdered form without changing the physical state of the particles to retain the discrete particulate character of each of said first and second quantities of said particles, and in the absence of chemical reaction between said herbicidal agent and said solubilization medium to form a relatively uniform dry mixture thereof, there being a sufficient quantity of the phosphate medium in the dry blended mixture in relationship to the quantity of herbicidal combined therewith such that the dry blended powder mixture will dissolve in water during preparation of a herbicidal solution therefrom that contains an adequate proportion of the herbicidal agent to provide from about 0.1 to about 2½% by weight of the active herbicidal agent in the herbicidal solution.

15. An herbicide as set forth in claim 14 wherein the dry blended admixture includes a mixture of substituted phenoxy acid and substituted benzoic acid herbicides.

16. An herbicide as set forth in claim 14 wherein said active substituted phenoxy acid herbicidal agent is 2,4-dichlorophenoxy acetic acid.

17. An herbicide as set forth in claim 14 wherein said active substituted phenoxy acid herbicidal agent is 4-(2,4-dichlorophenoxy)butanoic acid.

18. An herbicide as set forth in claim 14 wherein active substituted phenoxy acid herbicidal agent is (±)-2-(4-chloro-2-methylphenoxy)propanoic acid.

19. An herbicide as set forth in claim 14 wherein said active substituted phenoxy acid herbicidal agent is (4-chloro-2-methylphenoxy)acetic acid.

20. An herbicide as set forth in claim 14 wherein said active substituted phenoxy acid herbicidal agent is (±)-2-(2,4-dichlorophenoxy)propanoic acid.

21. An herbicide as set forth in claim 14 wherein said active substituted benzoic acid herbicidal agent is 3,6-dichloro-2-methoxybenzoic acid.

22. An herbicide as set forth in claim 14 wherein said active substituted benzoic acid herbicidal agent is 3-amino-2,5-dichlorobenzoic acid.

23. A composition as set forth in claim 14 wherein a sufficient quantity of the phosphate medium is present in the dry blended mixture to provide at least about 1.15 moles of the medium for each mole of active herbicidal agent in the initially dry blended mixture.

24. A composition as set forth in claim 14 wherein is included a mixture of said herbicidally active agents which are dry blended with the phosphate medium.

25. A composition as set forth in claim 14 wherein is included an anti-caking agent relatively uniformally distributed throughout the dry blended mixture.

26. A dry, water-soluble substituted phenoxy and/or benzoic acid herbicide powder composition consisting essentially of;

a dry blended mixture on a parts by weight basis of about
32 parts of dry, solid powder particles of 2,4-D,
15 parts of dry, solid powder particles of MCPP,
3 parts of dry, solid powder particles of dicamba, and
45 parts of diammonium phosphate said 2,4-D, MCPP, dicamba and diammonium phosphate having been dry blended in powdered form without changing the physical state of the particles to retain the discrete particulate character thereof, and in the absence of chemical reaction between said 2,4-D, MCPP and dicamba with the diammonium phosphate to form a relatively uniform dry mixture thereof.

27. A dry, water-soluble substituted phenoxy and/or benzoic acid herbicide powder composition consisting essentially of;

a dry blended mixture on a parts by weight basis of about
31 parts of dry, solid powder particles of 2,4-D,
16 parts of dry, solid powder particles of MCPP,
3 parts of dry, solid particles of dicamba, and
46 parts of diammonium phosphate said 2,4-D, MCPP, dicamba and diammonium phosphate having been dry blended in powdered form without changing the physical state of the particles to retain the discrete particulate character thereof, and in the absence of chemical reaction between said 2,4-D, MCPP and dicamba with the diammonium phosphate to form a relatively uniform dry mixture thereof;

28. A dry, water-soluble substituted phenoxy acid herbicide powder composition consisting essentially of;

a dry blended mixture on a parts by weight basis of about 50 parts of dry, solid powder particles of MCPA, and 46 parts of diammonium phosphate said MCPA and diammonium phosphate having been dry blended in powdered form without changing the physical state of the particles to retain the discrete particulate character thereof, and in the absence of chemical reaction between said MCPA with the diammonium phosphate to form a relatively uniform dry mixture thereof.

29. A dry, water-soluble substituted benzoic acid herbicide powder composition consisting essentially of;

a dry blended mixture on a parts by weight basis of about 50 parts of dry, solid powder particles of dicamba, and 41 parts of diammonium phosphate said dicamba and diammonium phosphate having been dry blended in powdered form without changing the physical state of the particles to retain the discrete particulate character thereof, and in the absence of chemical reaction between said dicamba with the diammonium phosphate to form a relatively uniform dry mixture thereof.

30. A dry, water-soluble substituted phenoxy acid herbicide powder composition consisting essentially of;

a dry blended mixture on a parts by weight basis of about 50 parts of dry, solid powder particles of 2,4-D, and 46 parts of diammonium phosphate said 2,4-D and diammonium phosphate having been dry blended in powdered form without changing the physical state of the particles to retain the discrete particulate character thereof, and in the absence of chemical reaction between said 2,4-D with the diammonium phosphate to form a relatively uniform dry mixture thereof.

31. A dry, water-soluble substituted phenoxy acid herbicide powder composition consisting essentially of;

a dry blended mixture on a parts by weight basis of about 50 parts of dry, solid powder particles of MCPA, and
45 parts of disodium phosphate
said MCPA and disodium phosphate having been dry blended in powdered form without changing the physical state of the particles to retain the discrete particulate character thereof, and in the absence of chemical reaction between said MCPA with the disodium phosphate to form a relatively uniform dry mixture thereof.

* * * * *